US006979331B2

(12) United States Patent
Hintringer et al.

(10) Patent No.: US 6,979,331 B2
(45) Date of Patent: *Dec. 27, 2005

(54) ABLATION DEVICE FOR CARDIAC TISSUE, IN PARTICULAR FOR A CIRCULAR LESION AROUND A VESSEL ORIFICE IN THE HEART

(75) Inventors: Florian Hintringer, Ampass (AT); Wolfgang Geistert, Rheinfelden (DE)

(73) Assignee: Biotronik GmbH & Co. KG, Berlin (DE)

( * ) Notice: Subject to any disclaimer, the term of this patent is extended or adjusted under 35 U.S.C. 154(b) by 175 days.

This patent is subject to a terminal disclaimer.

(21) Appl. No.: 10/419,925

(22) Filed: Apr. 22, 2003

(65) Prior Publication Data
US 2003/0204187 A1    Oct. 30, 2003

(30) Foreign Application Priority Data
Apr. 24, 2002  (DE)  ............................... 102 18 427

(51) Int. Cl.[7] ............................................. A61B 18/18
(52) U.S. Cl. ......................................... 606/41; 606/49
(58) Field of Search .................................... 606/27–52

(56) References Cited

U.S. PATENT DOCUMENTS 5,239,999 A    8/1993  Imran 6,640,120 B1 *  10/2003  Swanson et al. ............ 600/374
6,764,486 B2 *   7/2004  Natale .......................... 606/41
6,771,996 B2 *   8/2004  Bowe et al. ................. 600/374

FOREIGN PATENT DOCUMENTS

| EP | 1 042 990 A1 | 10/2000 |
| WO | WO 95/15115 A1 | 6/1995 |
| WO | WO 95/31111 A1 | 11/1995 |
| WO | WO 98/49957 A1 | 11/1998 |
| WO | WO 01/37723 A2 | 5/2001 |
| WO | WO 01/37925 A2 | 5/2001 |

* cited by examiner

*Primary Examiner*—Linda C. M. Dvorak
*Assistant Examiner*—Aaron Roane
(74) *Attorney, Agent, or Firm*—Browdy and Neimark, PLLC

(57) ABSTRACT

An ablation device for cardiac tissue, in particular for forming a circular lesion around a vessel orifice in the heart, comprises
 a catheter which, in the region of its distal end, is provided with an abutment device for holding the distal end on a cardiac vessel orifice, and
 a linear ablation applicator which is disposed proximally or distally relative to the abutment device of the catheter and is movable from a straight passive position into a radially expanded, approximately circular-arc-type encircling ablation position.

8 Claims, 2 Drawing Sheets

ABLATION DEVICE FOR CARDIAC TISSUE, IN PARTICULAR FOR A CIRCULAR LESION AROUND A VESSEL ORIFICE IN THE HEART

BACKGROUND OF THE INVENTION

1. Field of the Invention

The invention relates to an ablation device for cardiac tissue, in particular for forming a circular lesion around a vessel orifice in the heart, comprising a catheter which, in the region of its distal end, is provided with an abutment device for holding the distal end on a cardiac vessel orifice.

2. Background Art

Regarding the background of the invention it can be stated that catheter ablation is a therapy that is used to an increasing degree to treat certain types of arrhythmia. In the process, a lesion—i.e., a denaturation of tissue along the line of a tissue scarring—is created with the aid of the ablation applicator of the catheter at a certain location in the myocardial tissue in order to sever the faulty electrical stimulus pathways at that location that are responsible for arrhythmia. The introduction of energy into the myocardial tissue via the ablation applicator, as a rule, takes place by means of ablation electrodes that operate with high-frequency current. Other forms of energy, such as microwave energies, high-energy direct current or, in principle, other denaturing mechanisms, such as freezing or chemicals (for example alcohol), may also he used for the ablation. The term "ablation applicator", as it is used in the present application also in connection with the subject matter of the invention, shall always mean all of the listed ablation options, with ablation electrodes representing the most common variant.

From a multitude of ablation catheter variants that are adapted to their respective purposes, WO 98/49957 A1, which discloses an ablation device for generating linear lesions between the orifice openings of two pulmonary veins into the atrium of the heart, has been selected as the prior art. According to the preamble of claim 1, a steerable catheter is provided, which carries, on its distal end, an abutment device in the form of a dilatable balloon to secure the catheter in the ostium of the pulmonary vein.

In this known ablation device the catheter serves not only for basic positioning of the ablation applicator, but it also carries, on its shank, the given ablation electrodes themselves. In this special design, the catheter shank, proximally relative to the ablation electrodes, can now be brought to the front of the orifice opening of a second pulmonary vein by means of a second guide so that the linearly aligned ablation electrodes come to rest on the connecting line between the two orifice openings of two adjacent pulmonary veins. In this manner, a linear lesion can reliably be applied between the two orifice openings.

Further embodiments of ablation catheters are for example shown in U.S. Pat. No. 5,239,999 A, WO 95/15115 A1 and WO 95/31111 A1, which disclose ablation electrodes in variably coiled or slightly bent shape.

Recent studies have shown that circular lesions around or at the orifices of the pulmonary veins (hereinafter: pv orifice) into the atrium have been successful, especially for treating the atrial fibrillation of the heart.

The known ablation devices are not practical for lesions of this shape, there being no or hardly any possibility of putting into practice an annular arrangement of the ablation electrodes around or at the pv orifice.

SUMMARY OF THE INVENTION

The invention has as its object to present an ablation device whereby a circular lesion around or at a vessel orifice in the heart can be formed in a manner that is reliable and with an application technique that is easy to perform.

According to the invention, a catheter with a linear ablation applicator is provided that is disposed proximally or distally relative to the abutment device of the catheter and can be taken from a straight passive position to a radially expanded, circular-arc-type encircling ablation position and is preferably displaceable axially relative to the abutment device.

The embodiment, according to the invention, of the catheter helps obtain reliable positioning by the ablation device being fixed in the vessel orifice. On the other hand, the ablation applicator, by its encircling in the way of a circular arc in the ablation position, is brought quasi shape-inherently into a correct position for applying the circular lesion, preferably when the applicator is disposed proximally in front of the abutment device around the vessel orifice. A high degree of application reliability is achieved, accompanied with corresponding improvement of the therapeutic success.

A preferred embodiment provides for a combination of two catheters, namely a steerable positioning catheter, the distal end of which is equipped with an abutment device, and an ablation catheter coupled there-with, the distal end of which holds the ablation applicator. This separation of functions renders the positioning catheter very compact and thus flexible and excellently steerable, which works especially in favour of possible positioning in vessel orifices.

The abutment device is preferably a dilatable balloon on the shank of the positioning catheter. The diameter of the balloon, in its inflated condition, must be suited to the diameter of the vessel involved i.e., it is in an order of magnitude of approximately 5 to 25 mm.

For coupling the positioning and the ablation catheter, provision can be made for guidance of the positioning catheter within the ablation catheter. In an alternative design in the way of a mono-rail guidance of a catheter on a guide wire, the distal end of the ablation catheter may be guided by two guide sleeves for displacement on the positioning catheter. The sleeves are disposed on both sides of the ablation applicator, it being possible, by axial displacement of the sleeves towards one another, to bring the ablation applicator into its ablation position, which is put into practice preferably by wire pull kinematics.

To aid in the creation of the circular-arc-type encircling ablation position, the ablation applicator is formed preferably by a multiple-electrode arrangement, the individual electrodes of which, which are aligned in the axial direction, are composed of a highly flexible material—for example of one spiral winding per electrode, or of a flexible, conducting plastic.

A coverage of at least 180° by the ablation applicator ensures that a completely closed circular lesion can be attained with only one rotation of the ablation catheter.

Even though this is not a direct object of the invention, it needs to be pointed out that in particular the steerable positioning catheter may be provided with known measures for controlling its correct position. The position may, for example, be controlled sonographically by means of an ultrasonic transducer disposed at the tip of the positioning catheter, or by means of a bipolar electrogram, which can be derived by means of a bipolar electrode arrangement at the tip of the positioning catheter. The positioning catheter may also incorporate additional lumen for injecting an X-ray contrast agent, which is injected via the lumen into the pulmonary vein for angiographic imaging.

Further characteristics, details and advantages of the invention will become apparent from the following description, in which embodiments of the object of the invention will be explained in detail, based on the attached drawings.

DESCRIPTION OF THE PREFERRED EMBODIMENTS

Figures 1, 2:
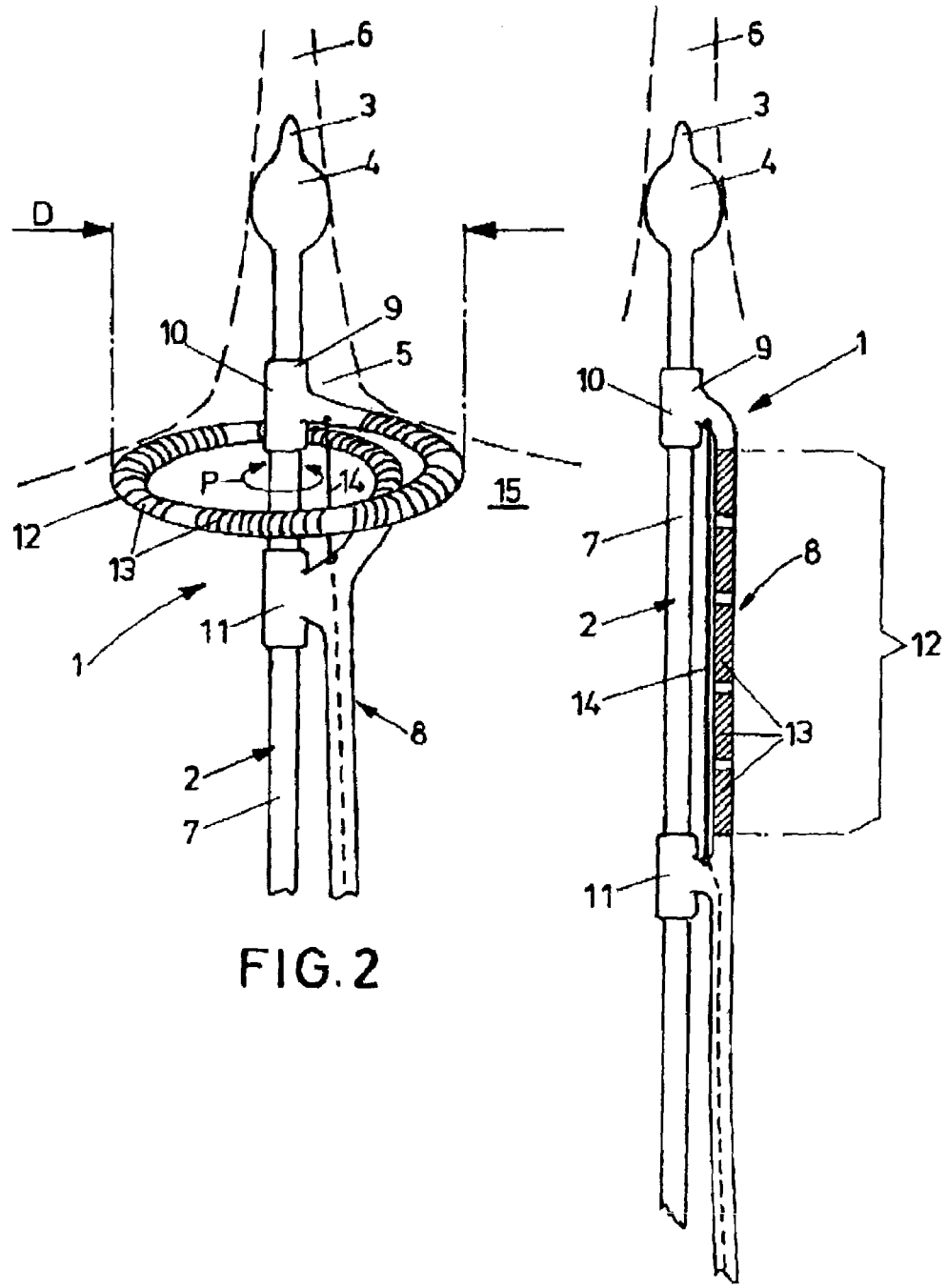
FIG. 1 is a schematic partial view of an ablation device in its passive position in a first embodiment.
FIG. 2 is an illustration, analogous to FIG. 1, of the device in the ablation position.
Figure 3:
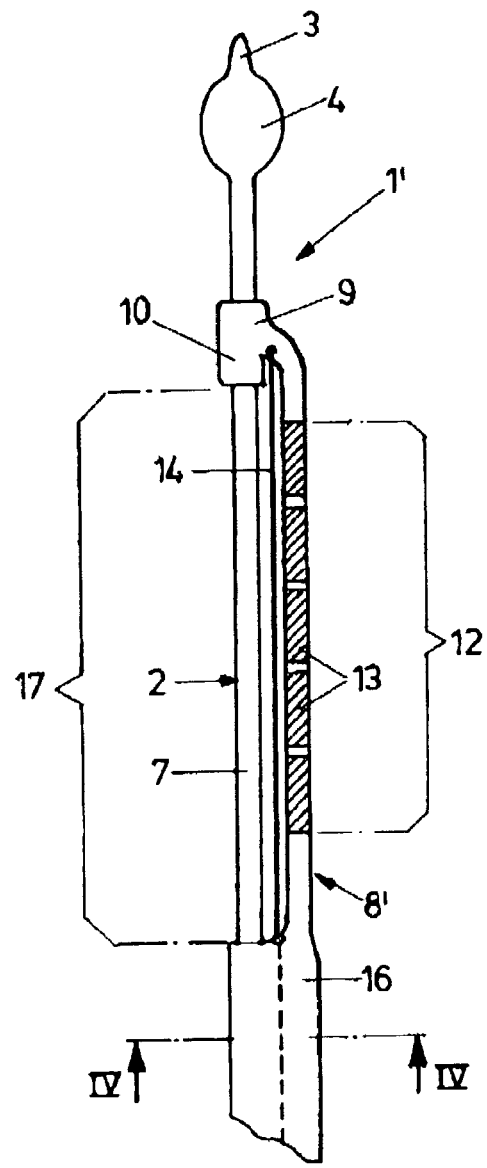
FIG. 3 is a diagrammatic view of details of a second embodiment of an ablation device in a passive position.

As becomes clear from FIG. 1, the ablation device, which has been marked in its entirety with the numeral 1, incorporates a steerable positioning catheter 2, which has in front of its distal end 3 a dilatable balloon 4. In FIGS. 1 to 3, the balloon 4 is shown in its expanded condition in which it fixes the distal end 3 of the catheter 2 in an orifice opening 5 of a pulmonary vein 6 (shown in a dashed line in FIG. 2) into the atrium of the heart. The positioning catheter 2 may be designed conventionally and ma) be provided, for example with a lumen for a guide wire, a deflection device for the targeted guiding of the distal end 3, etc. Other supplemental devices have furthermore already been mentioned in the introductory part of the specification.

An ablation catheter 8 is disposed on the shank 7 of the positioning catheter 2. For displaceable guidance of the ablation catheter 8 on the positioning catheter 2, provision is made for two guide sleeves 10, 11, which are formed on the distal end 9 or at a distance there-from by some centimetres in the proximal direction, and which may be shifted along the positioning catheter 2.

In the area between the two guide sleeves 10, 11, the ablation catheter 8 is provided with an ablation applicator 12 in the form of five aligned ring electrodes 13, each of which is composed of highly flexible spiral wire. Through these ring electrodes 13, high-frequency current can be emitted to the tissue that comes into contact with the ring electrodes, for a lesion to be produced.

FIG. 1 shows the straight position of the ablation applicator 12, from which it can be taken to the radially expanded ablation position shown in FIG. 2 with the aid of a wire pull 14 extending in the catheter 2. For this purpose the wire pull 14 is fixed in the region of the distal guide sleeve 10 and, in the region of the proximal guide sleeve 11, extends into the ablation catheter 8. By steadying motion on the wire pull 14 and by advancing the ablation catheter 8, the proximal guide sleeve 11 is shifted along the positioning catheter 2 in the distal direction so that the ablation catheter 8 expands in the region of the ablation applicator 12 and is brought into a circular-arc-type encircling configuration based on an appropriate pre-shaping of the ablation catheter 8. The ablation applicator 12, in the process, covers an angle at circumference P of more than 180° so that the ablation applicator 12, in this ablation position, extends over more than half of the circumference of the circular lesion to be formed.

The formation of the circular lesion shall briefly be illustrated below, with the aid of FIGS. 1 and 2. The positioning catheter 2, accordingly, is entered with a nondilated balloon 4 via a transseptal puncture into the left atrium of the heart where the orifices of all pulmonary veins are mapped by conventional means. After confirming the correct position of the distal end 3 of the positioning catheter 2 inside the orifice opening 5 of the desired pulmonary vein 6, the balloon 4 is dilated and the positioning catheter 2 is thus fixed in the orifice opening 5.

Then the ablation catheter 8 is advanced along the shank 7 of the positioning catheter 2 as far as into the position, seen in FIG. 1, in front of the distal end 3 of the positioning catheter 2. The ablation applicator 12 is positioned proximally before the balloon 4 in the vicinity of the atrium 15 in front of the orifice opening 5. By displacement of the ablation catheter 8 relative to the wire pull 14, the proximal guide sleeve 11 is pushed ahead and the ablation applicator 12 is moved into the ablation position according to FIG. 2, in which the ring electrodes 13, covering the angle at circumference P, rest on the endocardium in the atrium. By emittance of high frequency current, part of the circular lesion is obtained. As the case may be, the ablation applicator 12 is then partially moved into the passive position seen in FIG. 1, rotated by 180° and again expanded in the way of a circular arc into the ablation position seen in FIG. 2. Retracting, rotating and again advancing the applicator 12 is also possible in the bent condition. Thus, the ablation applicator 12 fits tightly on an area of the endocardium of the atrium where a lesion has not previously been applied. By renewed emittance of current, the circular lesion around the orifice opening 5 is completed.

The standard size of the left atrium of a heart is approximately 40 mm; however, it is distinctly higher in patients with atrial fibrillation, amounting to 60 mm and more; therefore (he effective diameter of the ablation applicator 12, in the ablation position 5, should range from 5 to 25 mm for small blood vessels (for instance the inferior pulmonary vein). In the case of enlarged atrial or pulmonary veins, effective diameters are in the range of 25 to 60 mm.

Figure 4:
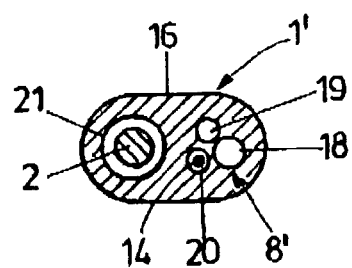
FIG. 4 is a section through the ablation device on the line IV—IV of FIG. 3.

In the embodiment, seen in FIGS. 3 and 4, of the ablation device 1', the design of the positioning catheter 2 is virtually unmodified; however, it is guided within the ablation catheter 8' in a lumen 21 provided in the widened portion 16. This portion 16 terminates proximally before the balloon 4 of the positioning catheter 2 by a gap 17. The ablation applicator 12 of the ablation catheter 8' is disposed within this gap 17. The ablation catheter 8' only comprises the distal guide sleeve 10, the job of the proximal guide sleeve 11 being fulfilled by the widened portion 16 enclosing the lumen 21.

Setting the ablation device according to FIG. 3 is put into practice by the positioning catheter 2 first being inserted and its balloon 4, by analogy to FIG. 2, being fixed in a pulmonary vein 6 as an abutment. Then the ablation catheter 8' is pushed ahead on the positioning catheter 2 as far as to the balloon 4 and the ablation applicator 12 is moved into the circular-arc-type encircling configuration by operation of the wire pull 14. In the process, the guide sleeve 10 is pulled against the widened portion 16 of the ablation catheter 8'. Then the entire ablation catheter 8' can be shifted along the positioning catheter 2 against the balloon 4 that works as an abutment, for the ablation electrodes 13 to be able to rest snugly on the vessel wall in the vicinity around a pulmonary vein orifice.

The sectional view according to FIG. 4 illustrates the lumen 21 with the positioning catheter 2. Furthermore, lines 18, 19 for electrode connections as well as a lumen 20 for the wire pull 14 are provided in the ablation catheter 8'.

What is claimed is:

1. An ablation device for cardiac tissue, in particular for forming a circular lesion around a vessel orifice (5) in the heart, comprising: a catheter (2) which, in the region of its distal end (3), is provided with an abutment device (4) for holding the distal end (3) in a cardiac vessel orifice (5); and a linear ablation applicator (12) which is disposed proximally relative to the abutment device (4) of the catheter (2) and is moveable from a straight passive position into a radially expanded, approximately circular-arc-type encircling ablation position, wherein the distal end (9) of the linear ablation applicator (12) is slidably engaged on the catheter (2), and wherein the abutment device is formed by a dilatable balloon (4) on a shank (7) of the catheter (2).

2. The ablation device according to claim 1, wherein the linear ablation applicator (12) is axially displaceable relative to the abutment device (4).

3. The ablation device according to claim 1, wherein said catheter (2) is a steerable positioning catheter, the distal end (3) of which is provided with the abutment device (4); and comprising an ablation catheter (8, 8'), which is coupled with the positioning catheter (2) and the distal end (9) of which is provided with the linear ablation applicator (12) which, in its ablation position, encircles the catheter (2) approximately in the way of a circular arc.

4. The ablation device according to claim 1, wherein directing the ablation applicator (12) from the passive into the ablation position is achievable by wire pull kinematics (14).

5. The ablation device according to claim 1, wherein the ablation applicator (12) is formed by a multiple-electrode arrangement, having individual electrodes (13) which are aligned in the axial direction and are composed of a highly flexible material.

6. The ablation device according to claim 1, wherein the ablation applicator (12), in a circular-arc-type encircling ablation position, covers an angle at circumference (P) of at least 180°.

7. An ablation device for cardiac tissue, in particular for forming a circular lesion around a vessel orifice (5) in the heart, comprising a steerable positioning catheter (2) which, in the region of its distal end (3), is provided with an abutment device (4) for holding the distal end (3) in a cardiac vessel orifice (5), a linear ablation applicator (12) which is disposed proximally relative to the abutment device (4) of the steerable positioning catheter (2) and is moveable from a straight passive position into a radially expanded, approximately circular-arc-type encircling ablation position, wherein the distal end (9) of the linear ablation applicator is slidably engaged on the steerable positiong catheter, and an ablation catheter (8, 8'), which is coupled with the steerable positioning catheter (2) and the distal end (9) of which is provided with the ablation applicator (12) which, in its ablation position, encircles positioning catheter (2) approximately in the way of a circular arc, wherein the steerable positioning catheter (2) is guided within a lumen (21) in a widened portion (16) of the ablation catheter (8'), the widened portion (16) terminating proximally before the abutment device (4) by a gap (17) and the ablation applicator (12) being disposed in the gap (17).

8. An ablation device for cardiac tissue, in particular for forming a circular lesion around a vessel orifice (5) in the heart, comprising a steerable positioning catheter (2) which, in the region of its distal end (3), is provided with an abutment device (4) for holding the distal end (3) in a cardiac vessel orifice (5)

a linear ablation applicator (12) which is disposed proximally in front of the abutment device (4) of the steerable positioning catheter (2) and is moveable from a straight passive position into a radially expanded, approximately circular-arc-type encircling ablation position, and an ablation catheter (8, 8'), which is coupled with the steerable positioning catheter (2), the distal end (9) of which is provided with the ablation applicator (12) which, in its ablation position, encircles steerable positioning catheter (2) approximately in the way of a circular arc, wherein the ablation catheter (8), at least in the region of its distal end, is movably guided on the steerable positioning catheter (2) by two guide sleeves (10, 11) which are disposed on either side of the ablation applicator (12) and, through axial displacement towards each other, move the ablation applicator (12) into the ablation position.

* * * * *